United States Patent
De Bokx et al.

[11] Patent Number: 5,745,543
[45] Date of Patent: Apr. 28, 1998

[54] APPARATUS FOR SIMULTANEOUS X-RAY DIFFRACTION AND X-RAY FLUORESCENCE MEASUREMENTS

[75] Inventors: Pieter K. De Bokx; Paul Van Der Sluis, both of Eindhoven; Bruno A. R. Vrebos, Almelo, all of Netherlands

[73] Assignee: U.S. Philips Corporation, NY, N.Y.

[21] Appl. No.: 722,649

[22] Filed: Sep. 30, 1996

[30] Foreign Application Priority Data

Oct. 3, 1995 [EP] European Pat. Off. ............. 95202647

[51] Int. Cl.⁶ .................................................. G01N 23/223
[52] U.S. Cl. .................................................. 378/45; 378/83
[58] Field of Search ..................... 378/45–49, 83

[56] References Cited

U.S. PATENT DOCUMENTS 4,800,580  1/1989  Houtman et al. .................... 378/83
5,406,608  4/1995  Yellepeddi et al. .................. 378/46

FOREIGN PATENT DOCUMENTS

0197157A1  10/1986  European Pat. Off. .

*Primary Examiner*—Craig E. Church
*Attorney, Agent, or Firm*—Anne E. Barschall

[57] ABSTRACT

In the case of simultaneous diffraction and fluorescence measurements in an apparatus for X-ray analysis comprising only one X-ray tube, a problem is encountered in that due to the presence of the collimators required for the fluorescence measurements only a very low X-ray power reaches the detectors, so that very long measuring times and/or an unfavorable signal-to-noise ratio occur. As a result, the detection limit for given measurements (low concentration of an element and/or light elements to be detected) becomes too high or the use of a (large and expensive) high-power X-ray tube is required. The invention utilizes a line focus tube 10 in combination with a single-slit collimator 14 for irradiating the sample 2, the fluorescence section 40 being constructed so as to have a plane or cylindrical analysis crystal 42 in combination with a location-sensitive detector 44. The diffraction measurements are performed by means of a conventional diffraction arrangement 24.

3 Claims, 1 Drawing Sheet

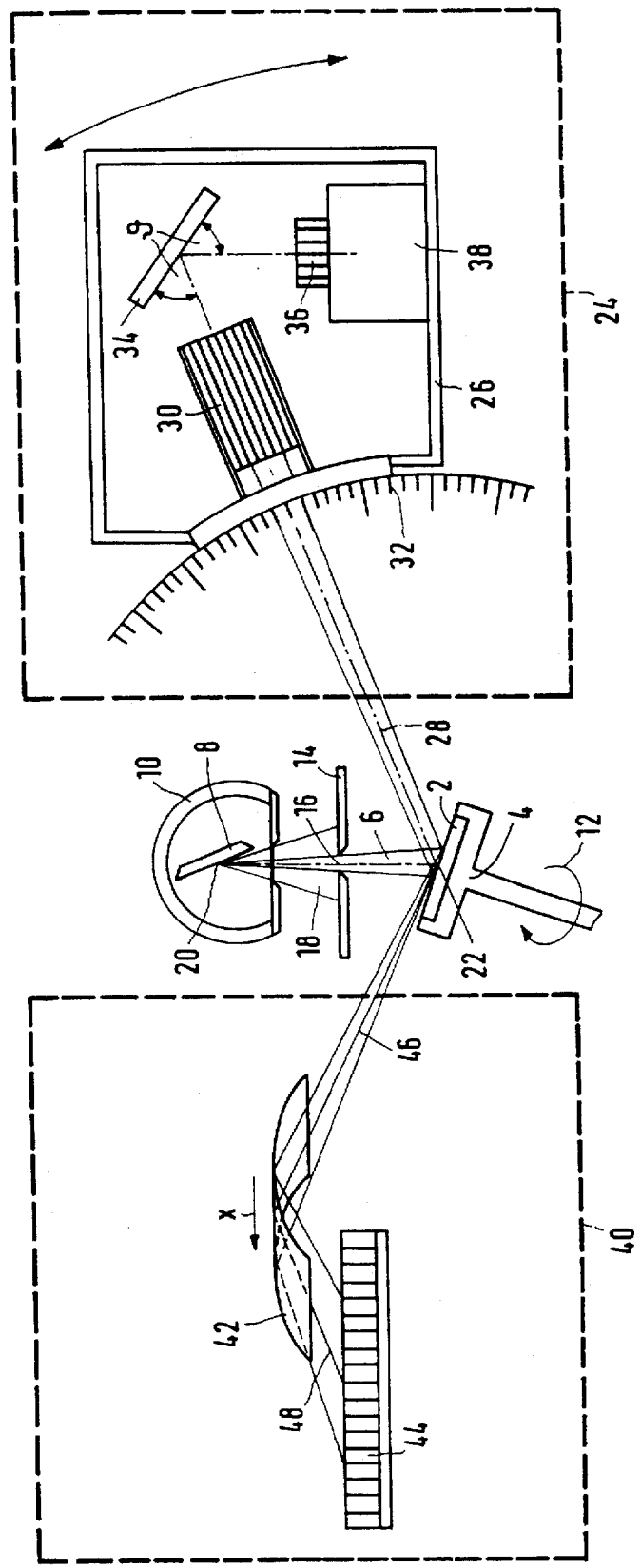

APPARATUS FOR SIMULTANEOUS X-RAY DIFFRACTION AND X-RAY FLUORESCENCE MEASUREMENTS

The invention relates to an apparatus for the examination of materials by simultaneous X-ray diffraction and X-ray fluorescence, comprising:

- sample location for accommodating a sample of the material to be examined,
- an X-ray source for irradiating the sample location by means of polychromatic X-rays,
- a collimator which is arranged to transmit at least one X-ray beam of line-shaped cross-section and is positioned between the X-ray source and the sample location,
- a diffraction unit which comprises a detection device for the detection of X-rays diffracted by the sample of the material to be examined, and
- a fluorescence unit which comprises a detection device with an analysis crystal for the detection of fluorescent radiation generated in the sample of the material to be examined.

An apparatus of this kind is known from European Patent Application 0 197 157.

In given circumstances it is desirable to utilize X-ray diffraction as well as X-ray fluorescence for X-ray analysis of materials. The determination of the presence of given chemical elements is then executed by means of X-ray fluorescence and the information concerning the structure of the material to be examined is obtained by X-ray diffraction. Notably in an industrial production environment, for example the production of concrete or crude iron or steel where the product quality is monitored by X-ray analysis, it is often necessary to examine many tens of material samples a day. Because a fluorescence measurement as well as a diffraction measurement may be time consuming (some tens of minutes, depending on the analysis to be carried out), in order to save time it is desirable to carry out the two types of measurement simultaneously. Moreover, it is desirable to execute such measurements by means of comparatively simple and inexpensive apparatus. Because the X-ray tube is an expensive component in such apparatus, it is particularly desirable to construct the analysis apparatus so as to include only one X-ray tube which is then used for fluorescence as well as for diffraction.

The X-ray source of the analysis apparatus disclosed in the cited Patent Application is formed an X-ray tube generating polychromatic X-rays consisting of a continuous spectrum on which a plurality of spectral lines characteristic of the anode material of the tube are superposed. The X-rays emanating from the X-ray tube are parallelized by a first Soller slit unit between the X-ray tube and the sample location. A Soller slit unit is a collimator consisting of a stack of a number of parallel plates of an X-ray absorbing material with a given (comparatively small) intermediate space. Via each intermediate space this type of collimator transmits only an X-ray beam having a substantially line-shaped cross-section, so that a parallelized X-ray beam is present beyond this collimator. Because parallelization of the X-ray beam takes place by selecting the radiation having the desired direction from the incident X-ray beam and by absorbing the radiation having an undesirable direction, such parallelization is accompanied by a substantial loss of X-ray power of the incident beam.

Even though no further information as regards the nature of the X-ray tube can be derived from the cited Patent document, to a person skilled in the art it will be evident that this X-ray tube is a fluorescence tube, i.e. an X-ray tube having an X-ray focus of comparatively large magnitude. This is why a Soller slit unit is required downstream from the tube, because otherwise the parallel radiation beam required for X-ray diffraction will not be obtained.

In the known apparatus the incident X-ray beam generates fluorescent radiation in the sample to be examined, which radiation is detected by a fluorescence unit which includes a detection unit with an analysis crystal. Between the sample and the analysis crystal there is arranged a second Soller slit unit and a third Soller slit unit is arranged between the analysis crystal and an X-ray detector provided in the detection device. Furthermore, in the sample in the known apparatus the incident beam is diffracted, so that the diffraction measurement can be performed simultaneously with the fluorescence measurement.

The analysis apparatus known from the cited Patent document is used to detect zinc in an iron environment, the zinc content being of the order of magnitude of from 70% to 95%. In that case the radiation yield from the zinc is always adequate, the more so because zinc is a comparatively heavy element with a high radiation yield. However, if this known apparatus were used for elements occurring in a substantially lower concentration and/or for lighter elements (such as elements from the series from sodium to iron), the concentration of these elements might be below the detection limit of the apparatus so that they could not be measured.

Furthermore, because of the presence of the first, the second and the third Soller slit unit, a very large part of the X-ray power produced by the X-ray tube will not be utilized for the benefit of the desired measurements, so that an X-ray tube having a comparatively high power is required. It is a drawback that such tubes are large and heavy, so that the construction of the supporting parts of the X-ray analysis apparatus must also be voluminous and heavy. Moreover, such X-ray tubes of comparatively high power also require a high cooling capacity, so that the volume of the apparatus is further increased. Furthermore, high absorptivity in the vicinity of the sample heats the measuring space and hence causes temperature gradients, affecting the accuracy of the measurements due to thermal expansions.

It is an object of the invention to provide an apparatus for the examination of materials by simultaneous X-ray diffraction and X-ray fluorescence in which a substantially lower detection limit can be achieved for a comparably high power of the X-ray tube.

To achieve this, the apparatus in accordance with the invention is characterized in that:

- the X-ray source is arranged to produce a line-shaped X-ray focus,
- the collimator comprises only one aperture which extends parallel to the line-shaped X-ray focus, and
- the detection device of the fluorescence unit comprises a location-sensitive detection array for the detection of X-rays reflected by the analysis crystal.

The invention is based on the recognition of the fact that in order to achieve X-ray diffraction with an acceptable resolution, the sample must be irradiated either by a parallel beam or by a beam having small dimensions at the area of the sample. (Actually, this is somewhat an oversimplification. In reality the beam must have a shape such that in any point of the beam which is not a collecting point (point or line focus) of the X-rays only one direction of these rays is present. It is then as if the beam originates from only one point or line, or converges to only one point or line, or is purely parallel. In that case it is said that the beam is correlated in at least one plane.) If preference is given to a line-shaped X-ray focus in combination with a line-shaped parallel collimator, line-shaped irradiation of the sample can be performed so that X-ray diffraction can be carried out with an acceptable resolution. A line-shaped X-ray focus, moreover, offers the advantage that the intensity is then maximum for a given, desired X-ray power. This can be explained on the basis of the fact that for a given X-ray power produced a line-shaped X-ray focus (having a given width) on the anode of the X-ray tube has a heat dissipation to the cooling environment which is better than that of a point-shaped X-ray focus (which point, however, has a finite spot dimension, so that it could better be called a circular disc). As a result, in the case of a line focus the X-ray power produced may be increased further than in the case of a point focus before reaching the power-limiting temperature on the anode, so that the intensity of a line-focus tube is optimum. The analysis crystal in the fluorescence unit serves for wavelength analysis of the fluorescent radiation in known manner, thus forming an intensity spectrum of this radiation. When such a crystal is irradiated from an area of comparatively small dimensions, like the line-shaped irradiation area according to the present invention, the wavelength of the radiation emanating from the analysis crystal is strongly correlated to the location. The invention utilizes this phenomenon by using a location-sensitive detection array in such a manner that each element of the array receives such a part of the X-rays reflected by the analysis crystal that it corresponds to a given wavelength of this radiation. The desired diffraction pattern and X-ray spectrum can thus be detected without substantial loss of X-rays generated by the X-ray source.

A simple geometry of the arrangement of the various components in the fluorescence unit is achieved by an embodiment of the invention in which the analysis crystal of the detection device is constructed as a flat crystal. A flat crystal is comparatively inexpensive and, moreover, a location-sensitive detection array situated in a flat plane can then also be used.

It is also possible to direct a larger part of the fluorescent radiation produced by the sample onto the location-sensitive detection array so that an X-ray tube having an even lower power can be used, if desired. In a further embodiment of the invention this is achieved in that the analysis crystal of the detection device of the fluorescence unit is constructed as a cylindrical surface. When the location-sensitive detection array is constructed so as to be comparatively narrow (i.e. in the direction of the line shape of the irradiation area on the sample), due to the focusing effect of the cylindrical analysis crystal in this direction a substantial part of the reflected X-rays can still be incident on the detection array.

The invention will be described in detail hereinafter with reference to a sole FIGURE. This FIGURE shows diagrammatically the arrangement of the relevant elements of an apparatus for X-ray analysis in accordance with the invention.

The FIGURE shows an apparatus for the examination of materials by simultaneous X-ray diffraction and X-ray fluorescence. The material to be examined is provided as a sample 2 on a sample carrier 4 which constitutes the sample location for accommodating a sample of the material to be examined. The sample consists of a powder or has an appearance which may be considered to be powdery for diffraction purposes, for example a metal sample consisting of one piece which is composed of a large number of comparatively small crystallites. The sample carrier 4 with the sample 2 can be made to rotate during the measurement, as denoted by the circular arrow 12, in order to even out inhomogeneities in the sample.

The sample location, i.e. the sample 2 present on the sample carrier 4, is irradiated by an X-ray beam 6 originating from the anode 8 of an X-ray tube 10. The X-ray beam 6 is a beam of polychromatic X-rays which consist of a continuous spectrum ("white" spectrum) on which there are superposed a plurality of spectral lines which are characteristic of the anode material of the tube. Known anode materials are copper (Cu), rhodium (Rh) and chromium (Cr). Generally speaking, the intensity of the characteristic lines is much higher than that of the white, continuous spectrum. The X-ray focus 20 is shaped as a line which extends perpendicularly to the plane of drawing in the FIGURE. This line has, for example a length/width ratio of approximately between 10:1 and 100:1.

Between the X-ray tube 10 and the sample carrier 4 there is arranged a collimator 14 which comprises a line-shaped aperture 16. This aperture stops the X-ray beam 18 from the X-ray tube to the beam 6, so that the dimensions of this aperture determine the dimensions of the line-shaped exposed region 22 on the sample. This region 22, extending perpendicularly to the plane of drawing like the line-shaped focus 20, has a length of, for example 2 cm and a width of no more than a few hundreds of μm. For the sake of clarity the width of the opening 16 is drawn much larger in the FIGURE than it would be in reality.

The X-ray analysis apparatus shown in the FIGURE also comprises a diffraction unit 24. This unit comprises a detection device 26 for detecting X-rays diffracted by the sample 2. Using a goniometer 32, the detection device 26 is arranged so as to be rotatable, with respect to the exposed region 22 on the sample.

The diffracted X-rays are shaped as an X-ray beam 28 which enters the detection device 26 via a Soller slit unit 30. Any background radiation is removed from the diffracted beam 28 in the Soller slit unit and the beam is further parallelized, if necessary. Subsequent to the Soller slit unit 30, the X-ray beam is incident on a monochromator crystal 34. This crystal selects the wavelength of the desired spectral line from the radiation produced by the X-ray tube. This is because a wide range of wavelengths is present in this radiation because the sample is irradiated by polychromatic X-rays. Moreover, this monochromator crystal is capable of separating two closely situated spectral lines, such as the $K\alpha_1$ line and the $K\alpha_2$ line of copper. However, this monochromator can also be dispensed with if the spectral line to be used has an intensity which is much higher than that of the continuous spectrum, so that the latter does not interfere with the determination of the angular position of the diffracted beam with the wavelength of said line.

For the purpose of detection, the radiation selected by the monochromator crystal is reflected by the monochromator 34 to an X-ray detector 38 via a Soller slit unit 36 which is provided for two reasons. The first reason is the removal of any background radiation. The second reason relates to the fact that the sample is irradiated in a line-shape. As is known, a powdery sample emits a number of diffracted beams in the case of point-like irradiation, said beams being shaped as concentric surfaces of cone whose apex is situated in the point of irradiation. Each point of the line at which the sample is exposed thus constitutes the apex of a set of cones, so that the line at which exposure takes place produces a series of adjacently situated "spread" cones. The section of this series of conical surfaces in a plane parallel to the cone axes would not produce lines. This problem, being known as "axial divergence", is solved by the Soller slit unit 36. Even though the plates of the Soller slit unit 36 are symbolically shown to extend perpendicularly to the plane of drawing in the FIGURE, they must actually be arranged parallel to the plane of drawing in order to achieve the described effect.

The X-ray analysis apparatus shown in the FIGURE also comprises a fluorescence unit 40 which includes an analysis crystal 42 and a location-sensitive detection array 44 for the detection of fluorescent radiation generated in the sample of the material to be examined. The line-shaped exposure area 22 emits fluorescence radiation emanates, a part of which is formed by the beam 46 which diverges in two directions, i.e. in the plane of drawing as well as in the direction perpendicular thereto. This beam is captured by the analysis crystal 42 which has a cylindrical surface in the present embodiment. As a result of this shape it is achieved that a given degree of focusing of the beam 46 takes place in the direction perpendicular to the plane of drawing, so that an as large as possible part of this beam is incident on the detection array 44. However, the analysis crystal 42 may also be constructed so as to have a plane surface; in that case a comparatively wide detection array is required as otherwise a part of the reflected beam 48 will be incident adjacent the detection array.

The (known) effect of the analysis crystal 42 is based on the known Bragg relation $2d \cdot \sin\theta = n\lambda$ ($d$=spacing of the reflecting planes of the crystal, $\theta$=angle of incidence of the X-rays on the crystal planes, $n$=the order of the reflection, and $\lambda$=the wavelength of the X-rays). This relation demonstrates that only radiation which is incident on the crystal at the correct angle $\theta$ is reflected. Because the beam 46 contains a wide range of wavelengths (the sample is irradiated with a "white" spectrum), there will always be wavelengths which can be reflected. Each ray which emanates from the line-shaped exposure area 22 and is incident on the analysis crystal in a different location in the direction x, therefore, is also incident at a different angle $\theta$ and reflected at the same angle $\theta$. A relation thus exists between the angle $\theta$ and the location x on the crystal or (via the Bragg relation) between the wavelength and the location on the crystal. Because an unambiguous relation exists between the angle of incidence $\theta$ and the reflection angle (in the case of a crystal surface extending parallel to the reflecting crystal planes these angles are the same), a relation exists between the reflected wavelength and the location on the detection array. In each element of the array the intensity of the radiation incident thereon is determined; by reading all elements of the array, the intensity spectrum is obtained as a function of the wavelength of the fluorescent radiation.

The sample carrier 4 is preferably mounted so that the surface of the sample encloses a small angle (order of magnitude of 5°) with respect to the direction of the beam 46 to be extracted. Consequently, the line-shaped exposure area 22 on the sample is "seen" at a very acute angle from the analysis crystal 42, so that the width of this area is very small. Consequently, the width of the location-sensitive detection array 44 is also reduced proportionally, so that the resolution of the fluorescence unit 40 is substantially enhanced.

It is to be noted that even though the foregoing description mentions an analysis crystal, is not necessary to use an actual crystalline structure for this purpose. In the context of the present invention the term analysis crystal is to be understood to mean also a multilayer mirror for X-ray reflection or any other structure suitable for performing wavelength selection of X-rays.

We claim:

1. An apparatus for the examination of materials by simultaneous X-ray diffraction and X-ray fluorescence, comprising:

a sample location (4) for accommodating a sample (2) of the material to be examined, an X-ray source (10) for irradiating the sample holder (4) by means of polychromatic X-rays (6, 18), a collimator (14) which is arranged to transmit at least one X-ray beam of line-shaped cross-section and is positioned between the X-ray source (10) and the sample holder (4), a diffraction unit (24) which comprises a detection device (26) for the detection of X-rays (28) diffracted by the sample (2) of the material to be examined, and a fluorescence unit (40) which comprises a detection device with an analysis crystal (42) for the detection of fluorescent radiation (46) generated in the sample (2) of the material to be examined, characterized in that the X-ray source (10) is arranged to produce a line-shaped X-ray focus (20), the collimator (14) comprises only one aperture (16) which extends parallel to the line-shaped X-ray focus (20), and the detection device of the fluorescence unit (40) comprises a location-sensitive detection array (44) for the detection of X-rays (48) reflected by the analysis crystal (42).

2. An apparatus as claimed in claim 1, in which the analysis crystal (42) of the detection device of the fluorescence unit (40) is constructed so as to have a plane surface.

3. An apparatus as claimed in claim 1, in which the analysis crystal (42) of the detection device of the fluorescence unit (40) is constructed so as to have a cylindrical surface.

* * * * *